United States Patent [19]

Yoshida

[11] Patent Number: Plant 5,891

[45] Date of Patent: Feb. 24, 1987

[54] AFRICAN VIOLET NAMED TRACY

[76] Inventor: Eiichi Yoshida, P.O. Box 4836, Hayward, Calif. 94540-4836

[21] Appl. No.: 726,849

[22] Filed: Apr. 24, 1985

[51] Int. Cl.[4] ..... A01H 5/00

[52] U.S. Cl. ..... Plt./69

[58] Field of Search ..... Plt./69

*Primary Examiner*—Robert E. Bagwill

[57] ABSTRACT

A new variety of African violet plant for potted plant culture particularly distinguished by its year around blooming capability, its profuse production of small two-toned bouquet of flowers, and its compact growth with abundant foliage of solid green color.

1 Drawing Figure

BACKGROUND OF THE NEW PLANT

This new variety of African violet plant was discovered by me in 1983 after crossing Seed Parent Melodie Laura Ann and Melodie Mary Ann, at Hayward, Calif. With subsequent propagation of the new plant by means of leaf cuttings at Hayward, Calif., this plant has demonstrated that its distinctive characteristics hold true from generation to generation and appear to be firmly fixed.

DESCRIPTION AND ILLUSTRATION OF THE PLANT

The drawing is a full color photographic view of the plant in bloom, the colors shown being as nearly true as it is reasonably possible to obtain by conventional photographic procedures.

The following is a detailed description of my new African violet plant with the color designation being according to the R.H.S. Colour Chart published by The Royal Horticultural Society of London, England, with collaboration by The British Colour Council.

THE PLANT

Origin: Seedling, #H-375/5.
Seed parent: Melodie Laura Ann.
Pollen parent: Melodie Mary Ann.
Classification:
- *Botanic.*—*Saintpaulia ionanthe.*
- *Commercial.*—African Violet.

Form: Rosette arrangement.
Height: 8 to 11 cm. tall.
Growth: New growth is vigorous and has a tendency to grow slightly upwards. As leaves get older, they grow more horizontally and eventually grow somewhat downward.
Size: Medium; overall plant diameter is from 22 to 32.2 cm.
Mutation prone: Very little for foliage. An occasional solid flowering plant is produced.
Leaves: Brittle.
- *Shape.*—Oval.
- *Length.*—Approximately 6.7 cm. for a mature leaf.
- *Width.*—Approximately 5.7 cm. for a mature leaf.
- *Color.*—Upperside: Medium Green. Underside: Light Green.
- *Texture.*—Upperside: Pubescent. Underside: Puberulent.
- *Ribs and veins.*—Veins are pinnate, slightly sunken on leaf surface, pronounced on underside of leaf.

Petiole: Round, light green, pubescent on its upper and puberulent on its underside. Length varies with age of leaf and plant.
Flower:
- *Blooming habit.*—Continuous and abundant under optimum growing conditions.
- *Number.*—10 to 12 per peduncle.
- *Size.*—Each flower is approximately 2.6 cm. in diameter.
- *Color.*—White Group, 155-A. Center is Violet Group, 87-A, from the R.H.S. Colour Chart.
- *Type.*—Single.
- *Petals.*—5 per individual flower with smooth margins.
- *Texture.*—Smooth and flexible.
- *Appearance.*—Sparkly upper surface. Underside is shiny with small bumps and is finely puberulent.
- *Peduncles.*—Short, strong, pubescent, small amount of red pigment in pedicels.
- *Inflorescence.*—Cyme, upright, above foliage.
- *Calyx.*—Quinquepartite, puberulent, slightly red pigmented.
- *Persistence.*—Flowers do not drop. Old flowers dry on the stalk.
- *Fragrance.*—None.

Reproductive organs:
- *Stamens.*—Usually 2 per flower and joined at top of anthers.
- *Anthers.*—Visible, bright yellow, fade slightly as they get older; one on each filament.
- *Filaments.*—Approximately 0.2 cm. long.
- *Pollen.*—Light yellow, ripens before stigma.
- *Pistils.*—Normally 1 per flower.
- *Stigma.*—Usually visible and accessible. When receptive it becomes swollen and usually exudes a small drop of clear fluid.
- *Style.*—Approximately 0.6 cm. long.
- *Ovary.*—Superior.

This variety of African violet plant is very suited for potted plant culture and its year around blooming capability gives the plant a commercially attractive value. Flowers do not drop. This new African violet is a good producer that is fairly disease resistant. One of the most important characteristic of this variety of African violet is that of uniformity. Uniformity and reliability are found at every point in the growing of this variety. In plants initiated at one time from leaf cuttings, virtually all plantlets uniformly come up at the same time and bloom at the same time following the planting.

I claim:

1. An African violet plant having blossoms which are white with violet centers, profusely produced above abundant foliage.

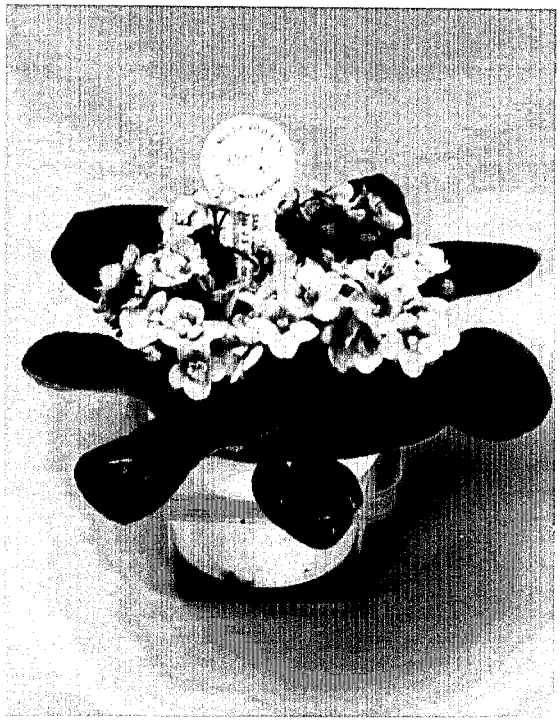

* * * * *